US009609867B2

(12) United States Patent
Mann et al.

(10) Patent No.: US 9,609,867 B2
(45) Date of Patent: Apr. 4, 2017

(54) SYNERGISTIC WEED CONTROL FROM APPLICATIONS OF HALOXYFOP AND ALS INHIBITOR HERBICIDES

(71) Applicant: Dow AgroSciences LLC, Indianapolis, IN (US)

(72) Inventors: Richard Kevin Mann, Franklin, IN (US); Yi-hsiou Huang, Pingtung Country (TW); Nelson M. Carranza Garzon, Ibague (CO)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/698,287

(22) Filed: Apr. 28, 2015

(65) Prior Publication Data
US 2015/0305335 A1 Oct. 29, 2015

Related U.S. Application Data

(60) Provisional application No. 61/984,957, filed on Apr. 28, 2014.

(51) Int. Cl.
*A01N 43/40* (2006.01)
*A01N 43/90* (2006.01)

(52) U.S. Cl.
CPC ............. *A01N 43/40* (2013.01); *A01N 43/90* (2013.01)

(58) Field of Classification Search
CPC ................................. A01N 43/40; A01N 43/90
See application file for complete search history.

(56) References Cited

U.S. PATENT DOCUMENTS

| 6,534,444 B1 | 3/2003 | Sievernich et al. |
| 7,842,646 B2 | 11/2010 | Sievernich et al. |
| 2012/0184437 A1 | 7/2012 | Mann et al. |
| 2013/0184156 A1* | 7/2013 | Mann ..................... A01N 43/88 504/132 |

OTHER PUBLICATIONS

Liu, C., Herbicidal Composition Useful for Preventing Annual Weeds in Soybean Fields, comprising Haloxyfop and Cloransulam-Methyl, CN 102273468, Derwent Abstract, 3 pages, Dec. 14, 2011.*
International Search Report and Written Opinion for Application No. PCT/US15/27940 Mailed on Jul. 14, 2015.

* cited by examiner

*Primary Examiner* — John Pak
*Assistant Examiner* — Andriae M Holt
(74) *Attorney, Agent, or Firm* — Michael J. Terapane; Meunier Carlin & Curfman, LLC

(57) ABSTRACT

Disclosed herein are herbicidal compositions comprising a synergistic, herbicidally effective amount of (a) haloxyfop or an agriculturally acceptable salt or ester thereof, and (b) an acetolactate synthase (ALS) inhibitor or an agriculturally acceptable salt or ester thereof. Also disclosed herein are methods of controlling undesirable vegetation which comprise applying to vegetation or an area adjacent the vegetation or applying to soil or water to prevent the emergence or growth of vegetation (a) haloxyfop or an agriculturally acceptable salt or ester thereof, and (b) an ALS inhibitor or an agriculturally acceptable salt or ester thereof, wherein (a) and (b) are each added in an amount sufficient to provide a synergistic herbicidal effect.

33 Claims, No Drawings

SYNERGISTIC WEED CONTROL FROM APPLICATIONS OF HALOXYFOP AND ALS INHIBITOR HERBICIDES

CROSS REFERENCE TO RELATED APPLICATIONS

This application claims the benefit of U.S. Provisional Patent Application Ser. No. 61/984,957 filed Apr. 28, 2014, which is expressly incorporated by reference herein.

FIELD OF THE DISCLOSURE

The present disclosure relates to herbicidal compositions comprising a synergistic, herbicidally effective amount of (a) haloxyfop or an agriculturally acceptable salt or ester thereof and (b) an acetolactate synthase (ALS) inhibitor or an agriculturally acceptable salt or ester thereof. The present disclosure also relates to methods for controlling undesirable vegetation.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Compositions comprising synergistically effective amounts of (a) haloxyfop or an agriculturally acceptable salt or ester thereof and (b) one or more acetolactate (ALS) inhibitors or an agriculturally acceptable salt or ester and methods of use thereof are described herein.

The weight ratio of (a) to (b) can be from 1:50 to 100:1 (e.g., from 1:20 to 6.4:1).

In some embodiments, (a) is haloxyfop-R-methyl. In some embodiments, (b) is selected from sulfonylurea herbicides, imidazolinone herbicides, triazolopyrimidine sulfonamide herbicides, pyrimidinyl oxybenzoate herbicides, sulfonylamino-carbonyl-triazolinone herbicides, anilide herbicides, or combinations thereof.

In some embodiments, (b) is a triazolopyrimidine sulfonamide herbicide. In some embodiments, the triazolopyrimidine sulfonamide herbicide is selected from cloransulam, diclosulam, florasulam, flumetsulam, metosulam, penoxsulam, pyroxsulam, and agriculturally acceptable salts and esters thereof, and combinations thereof.

In some embodiments, (b) is a pyrimidinyl oxybenzoate herbicide. In some embodiments, the pyrimidinyl oxybenzoate herbicide is selected from bispyribac, pyribenzoxim, pyriftalid, pyriminobac, pyrimisulfan, and agriculturally acceptable salts and esters thereof, and combinations thereof.

In some embodiments, (b) is a sulfonylurea herbicide, wherein (b) is not chlorimuron or thiameturon. In some embodiments, the sulfonylurea herbicide is selected from amidosulfuron, azimsulfuron, bensulfuron, chlorsulfuron, cinosulfuron, cyclosulfamuron, ethametsulfuron, ethoxysulfuron, flazasulfuron, flucetosulfuron, flupyrsulfuron, foramsulfuron, halosulfuron, imazosulfuron, iodosulfuron, iofensulfuron, mesosulfuron, metazosulfuron, metsulfuron, nicosulfuron, orthosulfamuron, oxasulfuron, primisulfuron, propyrisulfuron, prosulfuron, pyrazosulfuron, rimsulfuron, sulfometuron, sulfosulfuron, triasulfuron, tribenuron, trifloxysulfuron, triflusulfuron, tritosulfuron, and agriculturally acceptable salts and esters thereof, and combinations thereof.

In some embodiments, (b) is an imidazolinone herbicide. In some embodiments, the imidazolinone herbicide is selected from imazamethabenz, imazamox, imazapic, imazapyr, imazethapyr, and agriculturally acceptable salts and esters thereof, and combinations thereof.

In some embodiments, (b) is a sulfonylamino-carbonyl-triazolinone herbicide. In some embodiments, the sulfonylamino-carbonyl-triazolinone herbicide is selected from flucarbazone, propoxycarbazone, thiencarbazone, and agriculturally acceptable salts and esters thereof, and combinations thereof.

In some embodiments, (b) is an anilide herbicide. In some embodiments, the anilide herbicide is selected from triafamone.

In some embodiments, (b) is penoxsulam or an agriculturally acceptable salt thereof. In these embodiments, the weight ratio of (a) to (b) can be from 1:50 to 100:1 (e.g., from 1:50 to less than 1:2, from 5:2 to 4:1, or from 1:8 to 6.4:1). In some embodiments, (b) is bispyribac or an agriculturally acceptable salt or ester thereof. For example, (b) is bispyribac-sodium. In these embodiments, the weight ratio of (a) to (b) can be from 1:50 to 100:1 (e.g., from 1:10 to 3:1). In some embodiments, (b) is bensulfuron or an agriculturally acceptable salt or ester thereof. For example, (b) can include bensulfuron-methyl. In these embodiments, the weight ratio of (a) to (b) can be from 1:50 to 50:1 (e.g., from 1:20 to 1:1). In some embodiments, (b) is azimsulfuron or an agriculturally acceptable salt thereof. In these embodiments, the weight ratio of (a) to (b) can be from 1:50 to 100:1 (e.g., from 1:5 to 2:1).

In some embodiments, the composition further comprises an additional pesticide (e.g., bentazon, cyhalofop-butyl, oxyfluorfen, triclopyr, daimuron, fentrazamide, mefenacet, propanil, thiobencarb, fenoxaprop, profoxydim, sethoxydim, clethodim, quizalofop-P-ethyl and agriculturally acceptable salts and esters thereof, and combinations thereof). In some embodiments, the composition further comprises a herbicidal safener, an agriculturally acceptable adjuvant or carrier, or a combination thereof. The composition can be provided as a herbicidal concentrate.

Methods of controlling undesirable vegetation which comprise applying to vegetation or an area adjacent the vegetation or applying to soil or water to prevent the emergence or growth of vegetation (a) haloxyfop or an agriculturally acceptable salt or ester thereof and (b) an ALS inhibitor or an agriculturally acceptable salt or ester thereof, wherein (a) and (b) are each added in an amount sufficient to provide a synergistic herbicidal effect are also described. In some embodiments, (a) and (b) are applied simultaneously. In some embodiments, (a) and (b) are applied sequentially. In some embodiments, (a) and (b) are applied post-emergence of the undesirable vegetation.

In some embodiments, (a) is haloxyfop-R-methyl. In some embodiments, (b) is a sulfonylurea herbicide, an imidazolinone herbicide, a triazolopyrimidine sulfonamide herbicide, a pyrimidinyl oxybenzoate herbicide, an anilide herbicide, or combinations thereof.

In some embodiments, (b) is a triazolopyrimidine sulfonamide herbicide. In some embodiments, the triazolopyrimidine sulfonamide herbicide is selected from florasulam, penoxsulam, pyroxsulam, and agriculturally acceptable salts and esters thereof, and combinations thereof.

In some embodiments, (b) is a pyrimidinyl oxybenzoate herbicide. In some embodiments, the pyrimidinyl oxybenzoate herbicide is selected from bispyribac, pyribenzoxim, pyriftalid, pyriminobac, pyrimisulfan, and agriculturally acceptable salts and esters thereof, and combinations thereof.

In some embodiments, (b) is a sulfonylurea herbicide, wherein (b) is not chlorimuron or thiameturon. In some embodiments, the sulfonylurea herbicide is selected from azimsulfuron, bensulfuron, cinosulfuron, ethoxysulfuron, flazasulfuron, halosulfuron, imazosulfuron, iofensulfuron, metazosulfuron, metsulfuron, orthosulfamuron, propyrisulfuron, pyrazosulfuron, and agriculturally acceptable salts and esters thereof, and combinations thereof.

In some embodiments, (b) is an imidazolinone herbicide. In some embodiments, the imidazolinone herbicide is selected from imazamox, imazethapyr, and agriculturally acceptable salts and esters thereof, and combinations thereof.

In some embodiments, (b) is an anilide herbicide. In some embodiments, the anilide herbicide is selected from triafamone.

The undesirable vegetation can be a broadleaf weed, a grass weed, a sedge weed, or combinations thereof. In some embodiments, the undesirable vegetation includes red rice.

The undesirable vegetation can be controlled in a crop. In some embodiments, the crop in which undesirable vegetation is controlled is not pineapple. In some embodiments, the undesirable vegetation can be controlled in rice, vineyards, orchards, corn, cereals, sorghum, soybeans, cotton, sunflower, oilseed rape/canola, sugar beets, turf, range and pasture, industrial vegetation management (IVM), rights-of-way, or combinations thereof. In some embodiments, the undesirable vegetation can be controlled in a perennial plantation crop selected from palm, coffee, cocoa, rubber, and banana.

In some embodiments, the undesirable vegetation can be controlled in a crop that is acetyl coenzyme A carboxylase (ACCase)-tolerant, ALS (acetolactate synthase)-tolerant, or a combination thereof. In certain embodiments, the undesirable vegetation is controlled in rice that is resistant to, for instance, herbicides, pathogens, and/or insects (e.g., AAD-1 rice).

In some embodiments, (b) is penoxsulam or an agriculturally acceptable salt thereof. In some of these embodiments, (a) can be applied in an amount of from 2-200 grams active ingredient per hectare (g ai/ha; e.g., from 2-150 g ai/ha) and/or (b) can be applied in an amount of from 1-100 g ai/ha (e.g., from 5-32 g ai/ha). In these cases, the weight ratio of (a) to (b) can be from 1:50 to 100:1 (e.g., from 1:8 to 6.4:1).

In some embodiments, (b) is bispyribac or an agriculturally acceptable salt or ester thereof. For example, (b) is bispyribac-sodium. In some of these embodiments, (a) can be applied in an amount of from 2-200 g ai/ha (e.g., from 4-8 g ai/ha) and/or (b) can be applied in an amount of from 2-100 g ai/ha (e.g., from 2-40 g ai/ha). In these cases, the weight ratio of (a) to (b) can be from 1:50 to 100:1 (e.g., from 1:10 to 3:1).

In some embodiments, (b) is bensulfuron or an agriculturally acceptable salt or ester thereof. For example, (b) is bensulfuron-methyl. In some of these embodiments, (a) can be applied in an amount of from 2-200 g ai/ha (e.g., from 2-8 g ai/ha) and/or (b) can be applied in an amount of from 5-80 g ai/ha (e.g., from 10-40 g ai/ha). In these cases, the weight ratio of (a) to (b) can be from 1:50 to 50:1 (e.g., from 1:20 to 1:1).

In some embodiments, (b) is azimsulfuron or an agriculturally acceptable salt thereof. In some of these embodiments, (a) can be applied in an amount of from 2-200 g ai/ha (e.g., from 2-8 g ai/ha) and/or (b) can be applied in an amount of from 2-100 g ai/ha (e.g., from 10-40 g ai/ha). In these cases, the weight ratio of (a) to (b) can be from 1:50 to 100:1 (e.g., from 1:5 to 2:1).

The description below sets forth details of one or more embodiments. Other features, objects, and advantages will be apparent from the description and from the claims.

DETAILED DESCRIPTION

I. Definitions

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

As used herein, immature vegetation refers to small vegetative plants prior to reproductive stage, and mature vegetation refers to vegetative plants during and after the reproductive stage.

II. Synergistic Mixtures

Herbicidal compositions comprising a synergistic, herbicidally effective amount of (a) haloxyfop or an agriculturally acceptable salt or ester thereof and (b) one or more acetolactate (ALS) inhibitors or agriculturally acceptable salts or esters thereof and methods of use thereof are described herein.

A. Haloxyfop

The compositions described herein comprise haloxyfop or an agriculturally acceptable salt or ester thereof. Haloxyfop (i.e., 2-[4-[(3-chloro-5-trifluoromethyl-2-pyridyloxy)phenoxy]propionic acid) is a herbicide that inhibits the biosynthesis of lipids through inhibition of acetyl CoA carboxylase (ACCase). Haloxyfop can be used, for example, to control annual grasses in broad leaf crops. Its herbicidal activity is described in Tomlin, C. D. S., Ed. *The Pesticide Manual: A World Compendium*, 15$^{th}$ ed.; BCPC: Alton, 2009 (hereafter "*The Pesticide Manual*, Fifteenth Edition, 2009.")

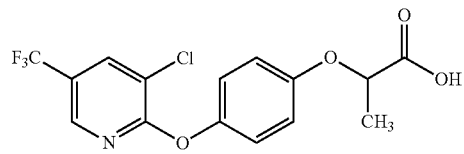 [SMILES: CC(Oc1ccc(Oc2ncc(C(F)(F)F)cc2Cl)cc1)C(=O)O]

Haloxyfop can be provided in its acid form (as shown above) or as an agriculturally acceptable salt or ester thereof. Exemplary agriculturally acceptable salts of haloxyfop include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_4$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, haloxyfop is provided as an agriculturally acceptable ester. Suitable esters include, but are not limited to, $C_1$-$C_4$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. Exemplary agriculturally acceptable esters of haloxyfop include haloxyfop-methyl, haloxyfop-etotyl, and haloxyfop-R-methyl.

Haloxyfop or agriculturally acceptable salts or esters thereof are or have been commercially available, for example, under the trademarks GALLANT SUPER® (by Dow AgroSciences LLC), HALCYON® (by Pacific Agriscience Pte. Ltd), GRANTE® (by Suzhou Eagro Ltd.), WOPRO-HALOXYFOP® (by B.V. Industrie- & Handelsonderneming Simonis), and IGNITE® (by Zelam Ltd.).

Haloxyfop or an agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the haloxyfop or agriculturally acceptable salt or ester thereof is applied to vegetation or an area adjacent the vegetation or applied to soil or water to prevent the emergence or growth of vegetation in an amount of 0.5 grams active ingredient per hectare (g ai/ha) or greater (e.g., 1 g ai/ha or greater, 1.5 g ai/ha or greater, 2 g ai/ha or greater, 2.5 g ai/ha or greater, 3 g ai/ha or greater, 3.5 g ai/ha or greater, 4 g ai/ha or greater, 4.5 g ai/ha or greater, 5 g ai/ha or greater, 7.5 g ai/ha or greater, 10 g ai/ha or greater, 12 g ai/ha or greater, 14 g ai/ha or greater, 15 g ai/ha or greater, 16 g ai/ha or greater, 18 g ai/ha or greater, 20 g ai/ha or greater, 22 g ai/ha or greater, 24 g ai/ha or greater, 25 g ai/ha or greater, 26 g ai/ha or greater, 28 g ai/ha or greater, 30 g ai/ha or greater, 32 g ai/ha or greater, 34 g ai/ha or greater, 35 g ai/ha or greater, 36 g ai/ha or greater, 38 g ai/ha or greater, 40 g ai/ha or greater, 42 g ai/ha or greater, 44 g ai/ha or greater, 45 g ai/ha or greater, 46 g ai/ha or greater, 48 g ai/ha or greater, 50 g ai/ha or greater, 52 g ai/ha or greater, 54 g ai/ha or greater, 55 g ai/ha or greater, 56 g ai/ha or greater, 58 g ai/ha or greater, 60 g ai/ha or greater, 62 g ai/ha or greater, 64 g ai/ha or greater, 65 g ai/ha or greater, 66 g ai/ha or greater, 68 g ai/ha or greater, 70 g ai/ha or greater, 72 g ai/ha or greater, 74 g ai/ha or greater, 75 g ai/ha or greater, 76 g ai/ha or greater, 78 g ai/ha or greater, 80 g ai/ha or greater, 81 g ai/ha or greater, 82 g ai/ha or greater, 84 g ai/ha or greater, 85 g ai/ha or greater, 86 g ai/ha or greater, 88 g ai/ha or greater, 90 g ai/ha or greater, 92 g ai/ha or greater, 94 g ai/ha or greater, 95 g ai/ha or greater, 96 g ai/ha or greater, 98 g ai/ha or greater, 100 g ai/ha or greater, 105 g ai/ha or greater, 110 g ai/ha or greater, 115 g ai/ha or greater, 120 g ai/ha or greater, 125 g ai/ha or greater, 130 g ai/ha or greater, 135 g ai/ha or greater, 140 g ai/ha or greater, 145 g ai/ha or greater, 150 g ai/ha or greater, 155 g ai/ha or greater, 160 g ai/ha or greater, 170 g ai/ha or greater, 180 g ai/ha or greater, or 190 g ai/ha or greater). In some embodiments, the haloxyfop or agriculturally acceptable salt or ester thereof is applied to vegetation or an area adjacent the vegetation or applied to soil or water to prevent the emergence or growth of vegetation in an amount of 200 g ai/ha or less (e.g., 195 g ai/ha or less, 190 g ai/ha or less, 180 g ai/ha or less, 170 g ai/ha or less, 160 g ai/ha or less, 155 g ai/ha or less, 150 g ai/ha or less, 145 g ai/ha or less, 140 g ai/ha or less, 135 g ai/ha or less, 130 g ai/ha or less, 125 g ai/ha or less, 120 g ai/ha or less, 115 g ai/ha or less, 110 g ai/ha or less, 105 g ai/ha or less, 100 g ai/ha or less, 98 g ai/ha or less, 96 g ai/ha or less, 95 g ai/ha or less, 94 g ai/ha or less, 92 g ai/ha or less, 90 g ai/ha or less, 88 g ai/ha or less, 86 g ai/ha or less, 85 g ai/ha or less, 84 g ai/ha or less, 82 g ai/ha or less, 81 g ai/ha or less, 80 g ai/ha or less, 78 g ai/ha or less, 76 g ai/ha or less, 75 g ai/ha or less, 74 g ai/ha or less, 72 g ai/ha or less, 70 g ai/ha or less, 68 g ai/ha or less, 66 g ai/ha or less, 65 g ai/ha or less, 64 g ai/ha or less, 62 g ai/ha or less, 60 g ai/ha or less, 58 g ai/ha or less, 56 g ai/ha or less, 55 g ai/ha or less, 54 g ai/ha or less, 52 g ai/ha or less, 50 g ai/ha or less, 48 g ai/ha or less, 46 g ai/ha or less, 45 g ai/ha or less, 44 g ai/ha or less, 42 g ai/ha or less, 40 g ai/ha or less, 38 g ai/ha or less, 36 g ai/ha or less, 35 g ai/ha or less, 34 g ai/ha or less, 32 g ai/ha or less, 30 g ai/ha or less, 28 g ai/ha or less, 26 g ai/ha or less, 25 g ai/ha or less, 24 g ai/ha or less, 22 g ai/ha or less, 20 g ai/ha or less, 18 g ai/ha or less, 16 g ai/ha or less, 15 g ai/ha or less, 14 g ai/ha or less, 12 g ai/ha or less, 10 g ai/ha or less, 7.5 g ai/ha or less, 5 g ai/ha or less, 4.5 g ai/ha or less, 4 g ai/ha or less, 3.5 g ai/ha or less, 3 g ai/ha or less, 2.5 g ai/ha or less, 2 g ai/ha or less, 1.5 g ai/ha or less, or 1 g ai/ha or less).

Haloxyfop or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the haloxyfop or agriculturally acceptable salt or ester thereof is applied to vegetation or an area adjacent the vegetation or applied to soil or water to prevent the emergence or growth of vegetation in an amount of from 0.5-200 g ai/ha (e.g., from 5-180 g ai/ha, from 10-160 g ai/ha, from 15-150 g ai/ha, from 18-140 g ai/ha). In some embodiments, the haloxyfop or agriculturally acceptable salt or ester thereof is applied in an amount from 5-32 g ai/ha.

B. ALS Inhibitors

In addition to haloxyfop, the compositions include one or more acetolactate synthase (ALS) inhibitors. ALS inhibitors disrupt the production of amino acids in the plant, which eventually leads to inhibition of DNA synthesis. ALS inhibitors include sulfonylureas, imidazolinones, triazolopyrimidine sulfonamides, pyrimidinyl oxybenzoates and sulfonylamino-carbonyl-triazolinones. In some embodiments, the composition can include an ALS inhibitor selected from sulfonylureas, imidazolinones, triazolopyrimidine sulfonamides, pyrimidinyl oxybenzoates, sulfonylamino-carbonyl-triazolinones and combinations thereof.

In some embodiments, (b) is a triazolopyrimidine sulfonamide herbicide. In some embodiments, the triazolopyrimidine sulfonamide herbicide is selected from cloransulam, diclosulam, florasulam, flumetsulam, metosulam, penoxsulam, pyroxsulam, and agriculturally acceptable salts and esters thereof, and combinations thereof.

In some embodiments, (b) is a pyrimidinyl oxybenzoate herbicide. In some embodiments, the pyrimidinyl oxybenzoate herbicide is selected from bispyribac, pyribenzoxim, pyriftalid, pyriminobac, pyrimisulfan, and agriculturally acceptable salts and esters thereof, and combinations thereof.

In some embodiments, (b) is a sulfonylurea herbicide, wherein (b) is not chlorimuron or thiameturon. In some embodiments, the sulfonylurea herbicide is selected from amidosulfuron, azimsulfuron, bensulfuron, chlorsulfuron, cinosulfuron, cyclosulfamuron, ethametsulfuron, ethoxysulfuron, flazasulfuron, flucetosulfuron, flupyrsulfuron, foramsulfuron, halosulfuron, imazosulfuron, iodosulfuron, iofensulfuron, mesosulfuron, metazosulfuron, metsulfuron, nicosulfuron, orthosulfamuron, oxasulfuron, primisulfuron, propyrisulfuron, prosulfuron, pyrazosulfuron, rimsulfuron, sulfometuron, sulfosulfuron, triasulfuron, tribenuron, trifloxysulfuron, triflusulfuron, tritosulfuron, and agriculturally acceptable salts and esters thereof, and combinations thereof.

In some embodiments, (b) is an imidazolinone herbicide. In some embodiments, the imidazolinone herbicide is selected from imazamethabenz, imazamox, imazapic, imazapyr, imazethapyr, and agriculturally acceptable salts and esters thereof, and combinations thereof.

In some embodiments, (b) is a sulfonylamino-carbonyltriazolinone herbicide. In some embodiments, the sulfonylamino-carbonyl-triazolinone herbicide is selected from flucarbazone, propoxycarbazone, thiencarbazone, and agriculturally acceptable salts and esters thereof, and combinations thereof.

In some cases, (b) is an anilide herbicide. In some embodiments, the anilide herbicide is selected from triafamone.

The (a) haloxyfop or an agriculturally acceptable salt or ester thereof is mixed with or applied in combination with (b) an ALS inhibitor or an agriculturally acceptable salt or ester thereof. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Tenth Edition, 2014, p. 487, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E = X + Y - \frac{X*Y}{100}$$

wherein

X=effect in percent (%) using (a) haloxyfop or an agriculturally acceptable salt or ester thereof at an application rate a;

Y=effect in % using (b) an ALS inhibitor or an agriculturally acceptable salt or ester thereof at an application rate b;

E=expected effect (in %) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of haloxyfop or an agriculturally acceptable salt or ester thereof and an ALS inhibitor or an agriculturally acceptable salt thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the ratio is from 1:50 to 100:1, such as from 1:40 to 90:1, from 1:30 to 80:1, from 1:25 to 70:1, from 1:20 to 60:1, from 1:20 to 50:1, from 1:20 to 40:1, from 1:20 to 30:1, from 1:20 to 20:1, from 1:10 to 15:1, from 1:10 to 10:1. In particular embodiments, the weight ratio of (a) haloxyfop or an agriculturally acceptable salt or ester thereof to (b) an ALS inhibitor or an agriculturally acceptable salt or ester thereof that is sufficient to induce a synergistic herbicidal effect is at least 1:50 (e.g., at least 1:45, at least 1:40, at least 1:35, at least 1:30, at least 1:25, at least 1:20, at least 1:15, at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 35:1, at least 40:1, at least 45:1, at least 50:1, at least 55:1, at least 60:1, at least 65:1, at least 70:1, at least 75:1, at least 80:1, at least 85:1, at least 90:1, or at least 95:1). In some embodiments, the weight ratio of (a) haloxyfop or an agriculturally acceptable salt or ester thereof to (b) an ALS inhibitor or an agriculturally acceptable salt or ester thereof that is sufficient to induce a synergistic herbicidal effect is less than 100:1 (e.g., less than 95:1, less than 90:1, less than 85:1, less than 80:1, less than 75:1, less than 70:1, less than 65:1, less than 60:1, less than 55:1, less than 50:1, less than 45:1, less than 40:1, less than 35:1, less than 30:1, less than 25:1, less than 20:1, less than 19:1, less than 18:1, less than 17:1, less than 16:1, less than 15:1, less than 14:1, less than 13:1, less than 12:1, less than 11:1, less than 10:1, less than 9:1, less than 8:1, less than 7:1, less than 6:1, less than 5:1, less than 4:1, less than 3:1, less than 2:1, less than 1:1, less than 1:2, less than 1:3, less than 1:4, less than 1:5, less than 1:6, less than 1:7, less than 1:8, less than 1:9, less than 1:10, less than 1:15, less than 1:20, less than 1:25, less than 1:30, less than 1:35, less than 1:40, or less than 1:45).

The weight ratio of (a) haloxyfop or an agriculturally acceptable salt or ester thereof to (b) an ALS inhibitor or an agriculturally acceptable salt or ester thereof that is sufficient to induce a synergistic herbicidal effect can range from any of the minimum ratios described above to any of the maximum values described above. In some embodiments, the weight ratio of (a) haloxyfop or an agriculturally acceptable salt or ester thereof to (b) an ALS inhibitor or an agriculturally acceptable salt or ester thereof that is sufficient to induce a synergistic herbicidal effect is from 1:50 to 100:1. In some embodiments, the weight ratio of (a) haloxyfop or an agriculturally acceptable salt or ester thereof to (b) an ALS inhibitor or an agriculturally acceptable salt or ester thereof can be in any of the following ranges: from 1:40 to 90:1; from 1:30 to 80:1; from 1:20 to 70:1; from 1:10 to 60:1; from 1:50 to 50:1; from 1:40 to 50:1; from 1:9 to 50:1; from 1:8 to 40:1; from 1:30 to 30:1; from 1:7 to 30:1; from 1:20 to 20:1; from 1:6 to 20:1; from 1:15 to 15:1; from 1:10 to 10:1; from 1:5 to 10:1; from 1:20 to 6.4:1; from 1:8 to 6.4:1; 1:5 to 5:1; from 1:4 to 5:1; from 1:10 to 4:1; from 1:10 to 3:1; from 1:20 to 2:1; from 1:5 to 2:1; from 1:20 to 1:1; from 1:2 to 1:1; or from 1:5 to 4:5.

The ALS inhibitor (or an agriculturally acceptable salt thereof) can be applied to vegetation or an area adjacent the vegetation or applied to soil or water to prevent the emergence or growth of vegetation in an amount sufficient to induce a herbicidal effect. In some embodiments, the ALS inhibitor or agriculturally acceptable salt thereof is applied to vegetation or an area adjacent the vegetation or applied to soil or water to prevent the emergence or growth of vegetation in an amount of 0.25 grams active ingredient per hectare (g ai/ha) or greater (e.g., 0.5 g ai/ha or greater, 1 g ai/ha or greater, 2 g ai/ha or greater, 3 g ai/ha or greater, 4 g ai/ha or greater, 5 g ai/ha or greater, 7.5 g ai/ha or greater, 10 g ai/ha or greater, 12 g ai/ha or greater, 14 g ai/ha or greater, 15 g ai/ha or greater, 16 g ai/ha or greater, 18 g ai/ha or greater, 20 g ai/ha or greater, 25 g ai/ha or greater, 30 g ai/ha or greater, 40 g ai/ha or greater, 50 g ai/ha or greater, 60 g ai/ha or greater, 70 g ai/ha or greater, 80 g ai/ha or greater, or 90 g ai/ha or greater). In some embodiments, the penoxsulam or agriculturally acceptable salt thereof is applied to vegetation or an area adjacent the vegetation or applied to soil or water to prevent the emergence or growth of vegetation in an amount of 100 g ai/ha or less (e.g., 90 g ai/ha or less, 80 g ai/ha or less, 70 g ai/ha or less, 60 g ai/ha or less, 50 g ai/ha or less, 40 g ai/ha or less, 30 g ai/ha or less, 25 g ai/ha or less, 20 g ai/ha or less, 18 g ai/ha or less, 16 g ai/ha or less, 15 g ai/ha or less, 14 g ai/ha or less, 12 g ai/ha or less, 10 g ai/ha or less, 7.5 g ai/ha or less, 5 g ai/ha or less, 4 g ai/ha or less, 3 g ai/ha or less, 2 g ai/ha or less or 1 g ai/ha or less).

In certain embodiments, the herbicidal composition comprises a synergistic, herbicidally effective amount of (a) haloxyfop or an agriculturally acceptable salt or ester thereof and (b) penoxsulam or an agriculturally acceptable salt thereof, bispyribac or an agriculturally acceptable salt or ester thereof, bensulfuron or an agriculturally acceptable salt or ester thereof, or azimsulfuron or an agriculturally acceptable salt thereof.

1. Penoxsulam

The compositions described herein can include the ALS inhibitor penoxsulam (i.e., 2-(2,2-difluoroethoxy)-N-(5,8-dimethoxy[1,2,4]triazolo[1,5-c]pyrimidin-2-yl)-6-trifluoromethyl)benzenesulfonamide) or an agriculturally acceptable salt thereof.

Penoxsulam, shown below, is a triazolopyrimidine sulfonamide herbicide that provides broad-spectrum control of many annual, biannual, and perennial weeds. Its herbicidal activity is described in The Pesticide Manual, Sixteenth Edition, 2012. Penoxsulam, as well as methods of preparing penoxsulam, are known in the art. See, for example, U.S. Pat. No. 6,303,814 to Johnson, et al.

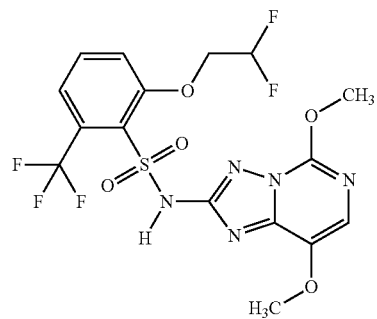 [SMILES: COc1cnc(OC)n2nc(NS(=O)(=O)c3c(OCC(F)F)cccc3C(F)(F)F)nc12]

In some embodiments, penoxsulam can be provided as an agriculturally acceptable salt of penoxsulam. Exemplary agriculturally acceptable salts of penoxsulam include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl) ammonium salts, olamine salts, and diglycolamine salts.

Penoxsulam can be used to control broadleaf weeds in, for instance, rice, corn, sorghum, wheat, barley and other cereal crops, lawns (e.g., residential, industrial, and institutional), golf courses, parks, cemeteries, athletic fields, sod farms, tree and vine crops, range and pasture, rights-of-way, roadsides, and other crop and non-crop uses. Its herbicidal activity is described in The Pesticide Manual, Fifteenth Edition, 2009. Penoxsulam is or has been commercially available, for example, from Dow AgroSciences LLC under the trademarks FENCER®, RICER®, VIPER®, CLIPPER®, SAPPHIRE®, WIDEATTACK®, GRASP®, and GRANITE®, and from SePRO Corporation under the trademark GALLEON®.

Penoxsulam or an agriculturally acceptable salt thereof can be applied to vegetation or an area adjacent the vegetation or applied to soil or water to prevent the emergence or growth of vegetation in an amount sufficient to induce a herbicidal effect. In some embodiments, the penoxsulam or agriculturally acceptable salt thereof is applied to vegetation or an area adjacent the vegetation or applied to soil or water to prevent the emergence or growth of vegetation in an amount of 0.5 grams active ingredient per hectare (g ai/ha) or greater (e.g., 1 g ai/ha or greater, 2 g ai/ha or greater, 3 g ai/ha or greater, 4 g ai/ha or greater, 5 g ai/ha or greater, 7.5 g ai/ha or greater, 10 g ai/ha or greater, 12 g ai/ha or greater, 14 g ai/ha or greater, 15 g ai/ha or greater, 16 g ai/ha or greater, 18 g ai/ha or greater, 20 g ai/ha or greater, 22 g ai/ha or greater, 24 g ai/ha or greater, 25 g ai/ha or greater, 26 g ai/ha or greater, 28 g ai/ha or greater, 30 g ai/ha or greater, 32 g ai/ha or greater, 34 g ai/ha or greater, 35 g ai/ha or greater, 36 g ai/ha or greater, 38 g ai/ha or greater, 40 g ai/ha or greater, 42 g ai/ha or greater, 44 g ai/ha or greater, 45 g ai/ha or greater, 46 g ai/ha or greater, 48 g ai/ha or greater, 50 g ai/ha or greater, 55 g ai/ha or greater, 60 g ai/ha or greater, 65 g ai/ha or greater, 70 g ai/ha or greater, 75 g ai/ha or greater, 80 g ai/ha or greater, 85 g ai/ha or greater, 90 g ai/ha or greater, or 95 g ai/ha or greater). In some embodiments, the penoxsulam or agriculturally acceptable salt thereof is applied to vegetation or an area adjacent the vegetation or applied to soil or water to prevent the emergence or growth of vegetation in an amount of 100 g ai/ha or less (e.g., 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 48 g ai/ha or less, 46 g ai/ha or less, 45 g ai/ha or less, 44 g ai/ha or less, 42 g ai/ha or less, 40 g ai/ha or less, 38 g ai/ha or less, 36 g ai/ha or less, 35 g ai/ha or less, 34 g ai/ha or less, 32 g ai/ha or less, 30 g ai/ha or less, 28 g ai/ha or less, 26 g ai/ha or less, 25 g ai/ha or less, 24 g ai/ha or less, 22 g ai/ha or less, 20 g ai/ha or less, 18 g ai/ha or less, 16 g ai/ha or less, 15 g ai/ha or less, 14 g ai/ha or less, 12 g ai/ha or less, 10 g ai/ha or less, 7.5 g ai/ha or less, 5 g ai/ha or less, 4 g ai/ha or less, 3 g ai/ha or less, 2 g ai/ha or less, or 1 g ai/ha or less).

Penoxsulam can be applied to vegetation or an area adjacent the vegetation or applied to soil or water to prevent the emergence or growth of vegetation in an amount ranging from any of the minimum values described above to any of the maximum values described above. In some embodiments, the penoxsulam or agriculturally acceptable salt thereof is applied to vegetation or an area adjacent the vegetation or applied to soil or water to prevent the emergence or growth of vegetation in an amount of from 1-100 g ai/ha (e.g., from 2-70 g ai/ha, from 3-60 g ai/ha, or from 4-50 g ai/ha). In some embodiments, the penoxsulam or agriculturally acceptable salt thereof is applied in an amount from 5-32 g ai/ha.

In some embodiments, (b) includes penoxsulam or an agriculturally acceptable salt thereof. In some embodiments, the weight ratio of (a) haloxyfop or an agriculturally acceptable salt or ester thereof to (b) penoxsulam or an agriculturally acceptable salt thereof that is sufficient to induce a synergistic herbicidal effect is at least 1:50 (e.g., at least 1:45, at least 1:40, at least 1:30, at least 1:20, at least 1:19, at least 1:18, at least 1:17, at least 1:16, at least 1:15, at least 1:14, at least 1:13, at least 1:12, at least 1:11, at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 5.1:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 20:1, at least 30:1, at least 40:1, at least 50:1, at least 60:1, at least 70:1, at least 80:1, or at least 90:1). In some embodiments, the weight ratio of (a) haloxyfop or an agriculturally acceptable salt or ester thereof to (b) penoxsulam or an agriculturally acceptable salt thereof that is sufficient to induce a synergistic herbicidal effect is less than 100:1 (e.g., less than 90:1, less than 80:1, less than 70:1, less than 60:1, less than 50:1, less than 40:1, less than 30:1, less than 25:1, less than 20:1, less than 19:1, less than 18:1, less than 17:1, less than 16:1, less than 15:1, less than 14:1, less than 13:1, less than 12:1, less than 11:1, less than 10:1, less than 9:1, less than 8:1, less than 7:1, less than 6:1, less than 5.1:1, less than 5:1, less than 4:1, less than 3:1, less than 2:1, less than 1:1, less than 1:2, less than 1:3, less than 1:4, less than 1:5, less than 1:6, less than 1:7, less than 1:8, less than 1:9, less than 1:10, less than 1:11, less than 1:12, less than 1:13, less than 1:14, less than 1:15, less than 1:16, less than 1:17, less than 1:18, less than 1:19, less than 1:20, less than 1:25, less than 1:30, less than 1:35, less than 1:40, or less than 1:45).

The weight ratio of (a) haloxyfop or an agriculturally acceptable salt or ester thereof to (b) penoxsulam or an agriculturally acceptable salt thereof can range from any of the minimum ratios described above to any of the maximum values described above. In some embodiments, the weight ratio of (a) haloxyfop or an agriculturally acceptable salt or ester thereof to (b) penoxsulam or an agriculturally acceptable salt thereof that is sufficient to induce a synergistic herbicidal effect is from 1:50 to 100:1 (e.g., from 1:18 to 10:1, or from 1:15 to 5.1:1).

In some embodiments, when (b) is penoxsulam, the weight ratio of (a) haloxyfop or an agriculturally acceptable salt or ester thereof to (b) penoxsulam or an agriculturally acceptable salt thereof is from 1:50 to less than 1:2. In some embodiments, when (b) is penoxsulam, the weight ratio of (a) haloxyfop or an agriculturally acceptable salt or ester thereof to (b) penoxsulam or an agriculturally acceptable salt thereof is from 5:2 to 4:1. In some embodiments, the weight ratio of (a) haloxyfop or an agriculturally acceptable salt or ester thereof to (b) penoxsulam or an agriculturally acceptable salt thereof is from 1:8 to 6.4:1.

2. Bispyribac

The compositions described herein can include bispyribac (i.e., 2,6-bis(4,6-dimethoxy-2-pyrimidinyl)oxy benzoic acid) or an agriculturally acceptable salt or ester thereof as the ALS inhibitor. Bispyribac, shown below, is a pyrimidinyl oxybenzoate herbicide that provides postemergence control of a wide range of weeds in rice fields. Bispyribac can also be used to control weeds in grasses (e.g., on golf courses and sod farms) and to control aquatic weeds in bayous, drainage ditches, lakes, marshes, non-irrigation canals, ponds, and reservoirs. Bispyribac, as well as methods of preparing bispyribac, are known in the art. Its herbicidal activity is described, for example, in *The Pesticide Manual*, Fifteenth Edition, 2009.

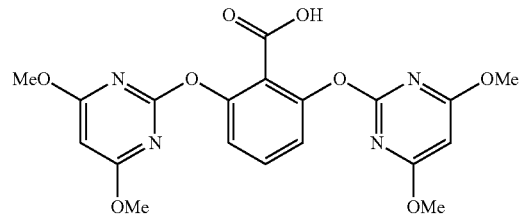 [SMILES: COc1cc(OC)nc(Oc2cccc(Oc3nc(OC)cc(OC)n3)c2C(=O)O)n1]

In some embodiments, bispyribac can be provided as an agriculturally acceptable salt of bispyribac. Exemplary agriculturally acceptable salts of bispyribac include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. Exemplary agriculturally acceptable salts of bispyribac include bispyribac-sodium. Bispyribac can also be provided as an agriculturally acceptable ester of bispyribac. Suitable bispyribac esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl.

Bispyribac or agriculturally acceptable salts or esters thereof are or have been commercially available, for example, under the trademarks AGRONOMENY® (by Agro-Care Chemical Industry Group Limited), ECTRAN® (by Ipesa S.A.), GRASS-SHORT®, NOMINEE®, REGIMENT®, and SHORT-KEEP® by Kumiai Chemical Industry Co., Ltd.), VIPER® (by Point Americas Inc.), SUNBISHI® (by Sundat Pte. Ltd.), REGIMENT®, TRADEWIND®, and VELOCITY® (by Valent U.S.A. Corporation), DALIA® (by Hektas Ticaret T.A.S.), DESIGNEE® (by Insecticidas Internacionales, C.A.), ARMY® (by Proficol), SAFA NOMINAL® (by SAFA TARIM A.S.), and WOPRO-BISPYRIBAC® (by B.V. Industrie- & Handelsonderneming Simonis).

Bispyribac or an agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the bispyribac or agriculturally acceptable salt or ester thereof is applied to vegetation or an area adjacent the vegetation or applied to soil or water to prevent the emergence or growth of vegetation in an amount of 2 grams active ingredient per hectare (g ai/ha) or greater (e.g., 3 g ai/ha or greater, 4 g ai/ha or greater, 5 g ai/ha or greater, 6 g ai/ha or greater, 7 g ai/ha or greater, 7.5 g ai/ha or greater, 8 g ai/ha or greater, 9 g ai/ha or greater, 10 g ai/ha or greater, 12 g ai/ha or greater, 14 g ai/ha or greater, 15 g ai/ha or greater, 16 g ai/ha or greater, 18 g ai/ha or greater, 20 g ai/ha or greater, 22 g ai/ha or greater, 24 g ai/ha or greater, 25 g ai/ha or greater, 26 g ai/ha or greater, 28 g ai/ha or greater, 30 g ai/ha or greater, 32 g ai/ha or greater, 34 g ai/ha or greater, 35 g ai/ha or greater, 36 g ai/ha or greater, 38 g ai/ha or greater, 40 g ai/ha or greater, 42 g ai/ha or greater, 44 g ai/ha or greater, 45 g ai/ha or greater, 46 g ai/ha or greater, 48 g ai/ha or greater, 50 g ai/ha or greater, 52 g ai/ha or greater, 54 g ai/ha or greater, 55 g ai/ha or greater, 56 g ai/ha or greater, 58 g ai/ha or greater, 60 g ai/ha or greater, 62 g ai/ha or greater, 64 g ai/ha or greater, 65 g ai/ha or greater, 66 g ai/ha or greater, 68 g ai/ha or greater, 70 g ai/ha or greater, 72 g ai/ha or greater, 74 g ai/ha or greater, 75 g ai/ha or greater, 76 g ai/ha or greater, or 78 g ai/ha or greater). In some embodiments, the bispyribac or agriculturally acceptable salt or ester thereof is applied to vegetation or an area adjacent the vegetation or applied to soil or water to prevent the emergence or growth of vegetation in an amount of 80 g ai/ha or less (e.g., 78 g ai/ha or less, 76 g ai/ha or less, 75 g ai/ha or less, 74 g ai/ha or less, 72 g ai/ha or less, 70 g ai/ha or less, 68 g ai/ha or less, 66 g ai/ha or less, 65 g ai/ha or less, 64 g ai/ha or less, 62 g ai/ha or less, 60 g ai/ha or less, 58 g ai/ha or less, 56 g ai/ha or less, 55 g ai/ha or less, 54 g ai/ha or less, 52 g ai/ha or less, 50 g ai/ha or less, 48 g ai/ha or less, 46 g ai/ha or less, 45 g ai/ha or less, 44 g ai/ha or less, 42 g ai/ha or less, 40 g ai/ha or less, 38 g ai/ha or less, 36 g ai/ha or less, 35 g ai/ha or less, 34 g ai/ha or less, 32 g ai/ha or less, 30 g ai/ha or less, 28 g ai/ha or less, 26 g ai/ha or less, 25 g ai/ha or less, 24 g ai/ha or less, 22 g ai/ha or less, 20 g ai/ha or less, 18 g ai/ha or less, 16 g ai/ha or less, 15 g ai/ha or less, 14 g ai/ha or less, 12 g ai/ha or less, 10 g ai/ha or less, 9 g ai/ha or less, 8 g ai/ha or less, 7.5 g ai/ha or less, 7 g ai/ha or less, 6 g ai/ha or less, 5 g ai/ha or less, 4 g ai/ha or less, or 3 g ai/ha or less).

Bispyribac or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the bispyribac or an agriculturally acceptable salt or ester thereof is applied to vegetation or an area adjacent the vegetation or applied to soil or water to prevent the emergence or growth of vegetation in an amount of from 2-100 g ai/ha (e.g., from 3-70 g ai/ha, from 5-60 g ai/ha, from 7-50 g ai/ha, or from 20-40 g ai/ha).

In some embodiments, (b) includes bispyribac or an agriculturally acceptable salt or ester thereof. For example, (b) can include bispyribac-sodium. In some embodiments, the weight ratio of (a) haloxyfop or an agriculturally acceptable salt or ester thereof to (b) bispyribac or an agriculturally acceptable salt or ester thereof that is sufficient to induce a synergistic herbicidal effect is at least 1:50 (e.g., at least 1:45, at least 1:40, at least 1:35, at least 1:30, at least 1:25, at least 1:20, at least 1:19, at least 1:18, at least 1:17, at least 1:16, at least 1:15, at least 1:14, at least 1:13, at least 1:12, at least 1:11, at least 1:10, at least 1:9, at least 1:8, at least 1:7, at least 1:6, at least 1:5, at least 1:4, at least 1:3, at least 2:5, at least 1:2, at least 3:5, at least 4:5, at least 1:1, at least 1.25:1, or at least 7:5.5, at least 1.5:1, at least 8:5, at least 3:1, at least 5:1, at least 10:1, at least 15:1, at least 20:1, at least 25:1, at least 30:1, at least 35:1, at least 40:1, at least 45:1, at least 50:1, at least 55:1, at least 60:1, at least 65:1, at least 70:1, at least 75:1, at least 80:1, at least 85:1, at least 90:1, or at least 95:1). In some embodiments, the weight ratio of (a) haloxyfop or an agriculturally acceptable salt or ester thereof to (b) bispyribac or an agriculturally acceptable salt or ester thereof that is sufficient to induce a synergistic herbicidal effect is less than 100:1 (e.g., less than 95:1, less than 90:1, less than 85:1, less than 80:1, less than 75:1, less than 70:1, less than 65:1, less than 60:1, less than 55:1, less than 50:1, less than 45:1, less than 40:1, less than 35:1, less than 30:1, less than 25:1, less than 20:1, less than 15:1, less than 10:1, less than 5:1, less than 3:1, less than 8:5. less than 1.5:1, less than 7:5, less than 1.25:1, less than 1:1, less than 4:5, less than 3:5, less than 1:2, less than 2:5, less than 1:3, less than 1:4, less than 1:5, less than 1:6, less than 1:7, less than 1:8, less than 1:9, less than 1:10, less than 1:11, less than 1:12, less than 1:13, less than 1:14, less than 1:15, less than 1:16, less than 1:17, less than 1:18, less than 1:19, less than 1:20, less than 1:25, less than 1:30, less than 1:35, less than 1:40, or less than 1:45).

The weight ratio of (a) haloxyfop or an agriculturally acceptable salt or ester thereof to (b) bispyribac or an agriculturally acceptable salt or ester thereof can range from any of the minimum ratios described above to any of the maximum values described above. In some embodiments, the weight ratio of (a) haloxyfop or an agriculturally acceptable salt or ester thereof to (b) bispyribac or an agriculturally acceptable salt or ester thereof that is sufficient to induce a synergistic herbicidal effect is from 1:50 to 100:1 (e.g., from 1:40 to 90:1, from 1:30 to 80:1, from 1:20 to 70:1 from 1:10 to 60:1, from 1:9 to 50:1, from 1:8 to 40:1, from 1:7 to 30:1, from 1:6 to 20:1, from 1:5 to 10:1, from 1:4 to 5:1, or from 1:5 to 2:1).

3. Bensulfuron

The compositions described herein can include bensulfuron (α-[(4,6-dimethoxypyrimidin-2-ylcarbamoyl)sulfamoyl]-o-toluic acid) or an agriculturally acceptable salt or ester thereof as the ALS inhibitor. Bensulfuron, shown below, is a sulfonylurea herbicide that provides selective control of broadleaf and sedge weeds in rice. Bensulfuron, as well as methods of preparing bensulfuron, are known in the art. Its herbicidal activity is described, for example, in *The Pesticide Manual*, Fifteenth Edition, 2009.

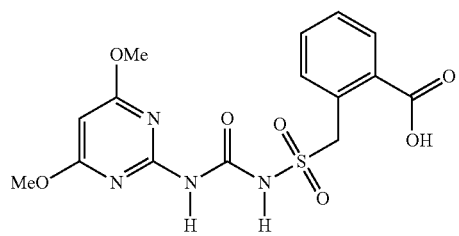 [SMILES: COc1cc(OC)nc(NC(=O)NS(=O)(=O)Cc2ccccc2C(=O)O)n1]

In some embodiments, bensulfuron can be provided as an agriculturally acceptable salt of bensulfuron. Exemplary agriculturally acceptable salts of bensulfuron include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl) ammonium salts, olamine salts, and diglycolamine salts. Bensulfuron can also be provided as an agriculturally acceptable ester of bensulfuron. Suitable bensulfuron esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. Exemplary agriculturally acceptable esters of bensulfuron include bensulfuron-methyl.

Bensulfuron or agriculturally acceptable salts or esters thereof are or have been commercially available, for example, under the trademarks ESCURI® (by Crystal Chemical Inter-America), PILARDAX® (by Pilar Agri-Science (Canada) Corp.), BIGBEN® (by Sulphur Mills Limited), LONDAX® (by United Phosphorus Ltd.), CONDAX® (by Zagro Singapore Pte. Ltd. and Agsin Pte. Ltd.), BELDAX® and SAFDAX® (by SAFA TARIM A.S.), and WOPRO-BENSULFURON® (by B.V. Industrie- & Handelsonderneming Simonis).

Bensulfuron or an agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the bensulfuron or agriculturally acceptable salt or ester thereof is applied to vegetation or an area adjacent the vegetation or applied to soil or water to prevent the emergence or growth of vegetation in an amount of 4 grams active ingredient per hectare (g ai/ha) or greater (e.g., 5 g ai/ha or greater, 6 g ai/ha or greater, 7 g ai/ha or greater, 7.5 g ai/ha or greater, 8 g ai/ha or greater, 9 g ai/ha or greater, 10 g ai/ha or greater, 12 g ai/ha or greater, 14 g ai/ha or greater, 15 g ai/ha or greater, 16 g ai/ha or greater, 18 g ai/ha or greater, 20 g ai/ha or greater, 22 g ai/ha or greater, 24 g ai/ha or greater, 25 g ai/ha or greater, 26 g ai/ha or greater, 28 g ai/ha or greater, 30 g ai/ha or greater, 32 g ai/ha or greater, 34 g ai/ha or greater, 35 g ai/ha or greater, 36 g ai/ha or greater, 38 g ai/ha or greater, 40 g ai/ha or greater, 42 g ai/ha or greater, 44 g ai/ha or greater, 45 g ai/ha or greater, 46 g ai/ha or greater, 48 g ai/ha or greater, 50 g ai/ha or greater, 52 g ai/ha or greater, 54 g ai/ha or greater, 55 g ai/ha or greater, 56 g ai/ha or greater, 58 g ai/ha or greater, 60 g ai/ha or greater, 62 g ai/ha or greater, 64 g ai/ha or greater, 65 g ai/ha or greater, 66 g ai/ha or greater, 68 g ai/ha or greater, 70 g ai/ha or greater, 72 g ai/ha or greater, 74 g ai/ha or greater, 75 g ai/ha or greater, 76 g ai/ha or greater, 80 g ai/ha or greater, 85 g ai/ha or greater, 90 g ai/ha or greater, or 95 g ai/ha or greater). In some embodiments, the bensulfuron or agriculturally acceptable salt or ester thereof is applied to vegetation or an area adjacent the vegetation or applied to soil or water to prevent the emergence or growth of vegetation in an amount of 100 g ai/ha or less (e.g., 95 g ai/ha or less, 90 g ai/ha or less, 85 g ai/ha or less, 80 g ai/ha or less, 78 g ai/ha or less, 76 g ai/ha or less, 75 g ai/ha or less, 74 g ai/ha or less, 72 g ai/ha or less, 70 g ai/ha or less, 68 g ai/ha or less, 66 g ai/ha or less, 65 g ai/ha or less, 64 g ai/ha or less, 62 g ai/ha or less, 60 g ai/ha or less, 58 g ai/ha or less, 56 g ai/ha or less, 55 g ai/ha or less, 54 g ai/ha or less, 52 g ai/ha or less, 50 g ai/ha or less, 48 g ai/ha or less, 46 g ai/ha or less, 45 g ai/ha or less, 44 g ai/ha or less, 42 g ai/ha or less, 40 g ai/ha or less, 38 g ai/ha or less, 36 g ai/ha or less, 35 g ai/ha or less, 34 g ai/ha or less, 32 g ai/ha or less, 30 g ai/ha or less, 28 g ai/ha or less, 26 g ai/ha or less, 25 g ai/ha or less, 24 g ai/ha or less, 22 g ai/ha or less, 20 g ai/ha or less, 18 g ai/ha or less, 16 g ai/ha or less, 15 g ai/ha or less, 14 g ai/ha or less, 12 g ai/ha or less, 10 g ai/ha or less, 9 g ai/ha or less, 8 g ai/ha or less, 7.5 g ai/ha or less, 7 g ai/ha or less, 6 g ai/ha or less, or 5 g ai/ha or less).

Bensulfuron or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the bensulfuron or an agriculturally acceptable salt or ester thereof is applied to vegetation or an area adjacent the vegetation or applied to soil or water to prevent the emergence or growth of vegetation in an amount of from 5-80 g ai/ha (e.g., from 6-70 g ai/ha, from 7-60 g ai/ha, from 8-50 g ai/ha, or from 10-40 g ai/ha).

In some embodiments, (b) includes bensulfuron or an agriculturally acceptable salt or ester thereof. For example, (b) can include bensulfuron-methyl. In some embodiments, the weight ratio of (a) haloxyfop or an agriculturally acceptable salt or ester thereof to (b) bensulfuron or an agriculturally acceptable salt or ester thereof that is sufficient to induce a synergistic herbicidal effect is at least 1:50 (e.g., at least 1:45, at least 1:40, at least 1:35, at least 1:30, at least 1:25, at least 1:20, at least 1:19, at least 1:18, at least 1:17, at least 1:16, at least 1:15, at least 1:14, at least 1:13, at least 1:12, at least 1:11, at least 1:10, at least 1:9, at least 1:8, at least 1:7, at least 1:6, at least 1:5, at least 1:4, at least 1:3, at least 2:5, at least 1:2, at least 3:5, at least 4:5, at least 1:1, at least 1.25:1, at least 7:5, at least 2:1, at least 3:1, at least 4:1, at least 5:1, at least 5.1:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 20:1, at least 30:1, or at least 40:1). In some embodiments, the weight ratio of (a) haloxyfop or an agriculturally acceptable salt or ester thereof to (b) bensulfuron or an agriculturally acceptable salt or ester thereof that is sufficient to induce a synergistic herbicidal effect is less than 50:1 (e.g., less than 40:1, less than 30:1, less than 20:1, less than 10:1, less than 7:1, less than 5:1, less than 4:1, less than 3:1, less than 2:1, less than 1.5:1, less than 7:5, less than 1.25:1, less than 1:1, less than 4:5, less than 3:5, less than 1:2, less than 2:5, less than 1:3, less than 1:4, less than 1:5, less than 1:6, less than 1:7, less than 1:8, less than 1:9, less than 1:10, less than 1:11, less than 1:12, less than 1:13, less than 1:14, less than 1:15, less than 1:16, less than 1:17, less than 1:18, less than 1:19, less than 1:20, less than 1:25, less than 1:30, less than 1:35, less than 1:40, or less than 1:45).

The weight ratio of (a) haloxyfop or an agriculturally acceptable salt or ester thereof to (b) bensulfuron or an agriculturally acceptable salt or ester thereof can range from any of the minimum ratios described above to any of the maximum values described above. In some embodiments, the weight ratio of (a) haloxyfop or an agriculturally acceptable salt or ester thereof to (b) bensulfuron or an agriculturally acceptable salt or ester thereof that is sufficient to induce a synergistic herbicidal effect is from 1:50 to 50:1 (e.g., from 1:20 to 2:1 or 1:2 to 1:1). In some embodiments, the weight ratio of (a) haloxyfop or an agriculturally acceptable salt or ester thereof to (b) bensulfuron or an agriculturally acceptable salt or ester thereof is from 1:2 to 2:1.

4. Azimsulfuron

The compositions described herein can include azimsulfuron (1-(4,6-dimethoxypyrimidin-2-yl)-3-[1-methyl-4-(2-methyl-2H-tetrazol-5-yl)pyrazol-5-ylsulfonyl]urea) or an agriculturally acceptable salt thereof as the ALS inhibitor. Azimsulfuron, shown below, is a sulfonylurea herbicide that can be used to control undesirable vegetation in paddy rice. Azimsulfuron, as well as methods of preparing azimsulfuron, are known in the art. Its herbicidal activity is described, for example, in *The Pesticide Manual*, Fifteenth Edition, 2009.

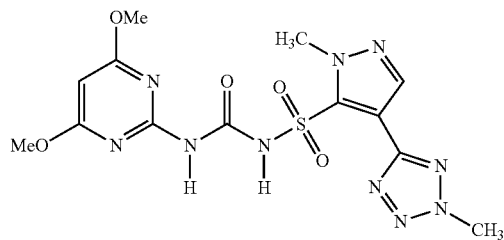 [SMILES: COc1cc(OC)nc(NC(=O)NS(=O)(=O)c2c(-c3nnn(C)n3)cnn2C)n1]

In some embodiments, azimsulfuron can be provided as an agriculturally acceptable salt of azimsulfuron. Exemplary agriculturally acceptable salts of azimsulfuron include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl) ammonium salts, olamine salts, and diglycolamine salts.

Azimsulfuron or agriculturally acceptable salts thereof are or have been commercially available, for example, under the trademark GULLIVER® by DuPont Crop Protection.

Azimsulfuron or an agriculturally acceptable salt thereof can be applied to vegetation or an area adjacent the vegetation or applied to soil or water to prevent the emergence or growth of vegetation in an amount sufficient to induce a herbicidal effect. In some embodiments, the azimsulfuron or agriculturally acceptable salt thereof is applied to vegetation or an area adjacent the vegetation or applied to soil or water to prevent the emergence or growth of vegetation in an amount of 5 grams active ingredient per hectare (g ai/ha) or greater (e.g., 6 g ai/ha or greater, 7 g ai/ha or greater, 7.5 g ai/ha or greater, 8 g ai/ha or greater, 9 g ai/ha or greater, 10 g ai/ha or greater, 12 g ai/ha or greater, 14 g ai/ha or greater, 15 g ai/ha or greater, 16 g ai/ha or greater, 18 g ai/ha or greater, 20 g ai/ha or greater, 22 g ai/ha or greater, 24 g ai/ha or greater, 25 g ai/ha or greater, 26 g ai/ha or greater, 28 g ai/ha or greater, 30 g ai/ha or greater, 32 g ai/ha or greater, 34 g ai/ha or greater, 35 g ai/ha or greater, 36 g ai/ha or greater, 38 g ai/ha or greater, 40 g ai/ha or greater, 42 g ai/ha or greater, 44 g ai/ha or greater, 45 g ai/ha or greater, 46 g ai/ha or greater, 48 g ai/ha or greater, 50 g ai/ha or greater, 52 g ai/ha or greater, 54 g ai/ha or greater, 55 g ai/ha or greater, 56 g ai/ha or greater, 58 g ai/ha or greater, 60 g ai/ha or greater, 62 g ai/ha or greater, 64 g ai/ha or greater, 65 g ai/ha or greater, 66 g ai/ha or greater, 68 g ai/ha or greater, 70 g ai/ha or greater, 72 g ai/ha or greater, 74 g ai/ha or greater, 75 g ai/ha or greater, 76 g ai/ha or greater, or 78 g ai/ha or greater). In some embodiments, the azimsulfuron or agriculturally acceptable salt thereof is applied to vegetation or an area adjacent the vegetation or applied to soil or water to prevent the emergence or growth of vegetation in an amount of 80 g ai/ha or less (e.g., 78 g ai/ha or less, 76 g ai/ha or less, 75 g ai/ha or less, 74 g ai/ha or less, 72 g ai/ha or less, 70 g ai/ha or less, 68 g ai/ha or less, 66 g ai/ha or less, 65 g ai/ha or less, 64 g ai/ha or less, 62 g ai/ha or less, 60 g ai/ha or less, 58 g ai/ha or less, 56 g ai/ha or less, 55 g ai/ha or less, 54 g ai/ha or less, 52 g ai/ha or less, 50 g ai/ha or less, 48 g ai/ha or less, 46 g ai/ha or less, 45 g ai/ha or less, 44 g ai/ha or less, 42 g ai/ha or less, 40 g ai/ha or less, 38 g ai/ha or less, 36 g ai/ha or less, 35 g ai/ha or less, 34 g ai/ha or less, 32 g ai/ha or less, 30 g ai/ha or less, 28 g ai/ha or less, 26 g ai/ha or less, 25 g ai/ha or less, 24 g ai/ha or less, 22 g ai/ha or less, 20 g ai/ha or less, 18 g ai/ha or less, 16 g ai/ha or less, 15 g ai/ha or less, 14 g ai/ha or less, 12 g ai/ha or less, 10 g ai/ha or less, 9 g ai/ha or less, 8 g ai/ha or less, 7.5 g ai/ha or less, 7 g ai/ha or less, or 6 g ai/ha or less).

Azimsulfuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the azimsulfuron or an agriculturally acceptable salt thereof is applied to vegetation or an area adjacent the vegetation or applied to soil or water to prevent the emergence or growth of vegetation in an amount of from 5-80 g ai/ha (e.g., from 7-70 g ai/ha, from 7.5-60 g ai/ha, from 8-50 g ai/ha, or from 10-40 g ai/ha).

In some embodiments, (b) includes azimsulfuron or an agriculturally acceptable salt thereof. In some embodiments, the weight ratio of (a) haloxyfop or an agriculturally acceptable salt or ester thereof to (b) azimsulfuron or an agriculturally acceptable salt thereof that is sufficient to induce a synergistic herbicidal effect is at least 1:50 (e.g., at least 1:45, at least 1:40, at least 1:35, at least 1:30, at least 1:25, at least 1:20, at least 1:19, at least 1:18, at least 1:17, at least 1:16, at least 1:15, at least 1:14, at least 1:13, at least 1:12, at least 1:11, at least 1:10, at least 1:9, at least 1:8, at least 1:7, at least 1:6, at least 1:5, at least 1:4, at least 1:3, at least 2:5, at least 1:2, at least 3:5, at least 4:5, at least 1:1, at least 1.25:1, at least 7:5, at least 2:1, at least 3:1, at least 4:1, at least 5:1, at least 5.1:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 20:1, at least 30:1, or at least 40:1). In some embodiments, the weight ratio of (a) haloxyfop or an agriculturally acceptable salt or ester thereof to (b) azimsulfuron or an agriculturally acceptable salt or ester thereof that is sufficient to induce a synergistic herbicidal effect is less than 100:1 (e.g., less than 95:1, less than 90:1, less than 80:1, less than 70:1, less than 60:1, less than 50:1, less than 40:1, less than 30:1, less than 20:1, less than 10:1, less than 7:1, less than 5:1, less than 4:1, less than 3:1, less than 2:1, less than 1.5:1, less than 7:5, less than 1.25:1, less than 1:1, less than 4:5, less than 3:5, less than 1:2, less than 2:5, less than 1:3, less than 1:4, less than 1:5, less than 1:6, less than 1:7, less than 1:8, less than 1:9, less than 1:10, less than 1:11, less than 1:12, less than 1:13, less than 1:14, less than 1:15, less than 1:16, less than 1:17, less than 1:18, less than 1:19, less than 1:20, less than 1:25, less than 1:30, less than 1:35, less than 1:40, or less than 1:45).

The weight ratio of (a) haloxyfop or an agriculturally acceptable salt or ester thereof to (b) azimsulfuron or an agriculturally acceptable salt thereof can range from any of the minimum ratios described above to any of the maximum values described above. In some embodiments, the weight ratio of (a) haloxyfop or an agriculturally acceptable salt or ester thereof to (b) azimsulfuron or an agriculturally acceptable salt thereof that is sufficient to induce a synergistic herbicidal effect is from 1:50 to 100:1 (e.g., from 1:30 to 30:1, from 1:20 to 20:1, from 1:5 to 2:1, or from 1:1 to 2:1).

III. Herbicidal Formulations

Haloxyfop and the one or more ALS inhibitors can be combined with one or more adjuvants and/or carrier to prepare a herbicidal formulation. In some embodiments, the formulation can be in the form of a single package formulation including both (a) haloxyfop or an agriculturally acceptable salt or ester thereof and (b) one or more ALS inhibitors or an agriculturally acceptable salt or ester thereof. In some embodiments, the formulation can be in the form of a single package formulation including both (a) and (b) and further including at least one additive, adjuvant, and/or carrier. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) haloxyfop or an agriculturally acceptable salt or ester thereof and/or (b) an ALS inhibitor or an agriculturally acceptable salt or ester thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the haloxyfop or agriculturally acceptable salt or ester thereof. In some embodiments, the additive is premixed with the ALS inhibitor or agriculturally acceptable salt or ester thereof. In some embodiments, the additive is premixed with the haloxyfor or agriculturally acceptable salt or ester thereof and the ALS inhibitor or agriculturally acceptable salt or ester thereof.

In some embodiments, the additive is an additional pesticide. For example, the compositions described herein can be applied in conjunction with one or more additional herbicides to control undesirable vegetation. The composition can be formulated with the one or more additional herbicides, tank mixed with the one or more additional herbicides, or applied sequentially with the one or more additional herbicides. Exemplary additional herbicides include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, 4-aminopicolinic acid based herbicides, such as halauxifen, halauxifen-methyl, and those described in U.S. Pat. Nos. 7,314,849 and 7,432,227 to Balko, et al., aminopyralid, amiprofos-methyl, amitrole, ammonium sulfamate, anilofos, anisuron, asulam, atraton, atrazine, azafenidin, aziprotryne, barban, BCPC, beflubutamid, benazolin, bencarbazone, benfluralin, benfuresate, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cisanilide, clacyfos, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, fluazifop, fluazifop-P-butyl, fluazolate, flucarbazone, flucetosulfuron, fluchloralin, flufenacet, flufenican, flufenpyrethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, fluroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halosafen, haloxydine, hexachloroacetone, hexaflurate, hexazinone, imazamethabenz, imazapic, imazapyr, imazaquin, indanofan, indaziflam, iodobonil, iodomethane, iodosulfuron, iodosulfuron-ethyl-sodium, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metflurazon, methabenzthiazuron, methalpropalin, methazole, methiobenzuron, methiozolin, methiuron, methometon, methoprotryne, methyl bromide, methyl isothiocyanate, methyldymron, metobenzuron, metobromuron, metolachlor, metosulam, metoxuron, metribuzin, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, oryzalin, oxadiargyl, oxadiazon, oxapyrazon, oxasulfuron, oxaziclomefone, oxyfluorfen, paraflufenethyl, parafluron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazoxyfen, pyributicarb, pyriclor, pyridafol, pyridate, pyrithiobac-sodium, pyroxasulfone, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thiobencarb, tiafenacil, tiocarbazil, tioclorim, tolpyralate, topramezone, tralkoxydim, tri-allate, triasulfuron, triaziflam, tribenuron, tribenuron-methyl, tricamba, triclopyr choline salt, triclopyr esters and amines, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, xylachlor and salts, esters, optically active isomers, and mixtures thereof.

In certain embodiments, the additional pesticide includes bentazone, cyhalofop (e.g., cyhalofop-butyl), oxyfluorfen, triclopyr, acetochlor, clopyralid, daimuron, fentrazamide, mefenacet, propanil, thiobencarb, agriculturally acceptable salts and esters thereof, and combinations thereof.

In some embodiments, the additional pesticide or an agriculturally acceptable salt or ester thereof is provided in a premixed formulation with (a), (b), or combinations thereof. In some embodiments, the haloxyfop or an agriculturally acceptable salt or ester thereof is provided in a premixed formulation with an additional pesticide. Exemplary premixes of haloxyfop or an agriculturally acceptable salt or ester thereof and an additive that are or have been commercially available include, but are not limited to, VULKAN ULTRA® (a premix incorporating bentazone by BASF Corporation).

In some embodiments, the penoxsulam or an agriculturally acceptable salt thereof is provided in a premixed formulation with an additional pesticide. In some embodiments, the penoxsulam or an agriculturally acceptable salt thereof is premixed with cyhalofop-butyl, oxyfluorfen, triclopyr, or combinations thereof. Exemplary premixes of penoxsulam or an agriculturally acceptable salt thereof and an additive that are or have been commercially available include, but are not limited to, CLINTON® (a premix incorporating cyhalofop-butyl by Dow AgroSciences LLC), REBELEX® (a premix incorporating cyhalofop-butyl by Dow AgroSciences LLC), PINDAR GT® (a premix incorporating oxyfluorfen by Dow AgroSciences LLC), and GRASP XTRA® (a premix incorporating triclopyr by Dow AgroSciences LLC).

In some embodiments, the bensulfuron or an agriculturally acceptable salt or ester thereof is provided in a premixed formulation with an additional pesticide. In some embodiments, the bensulfuron or an agriculturally acceptable salt thereof is premixed with acetochlor, clopyralid, mefenacet, daimuron, fentrazamide, thiobencarb, propanil, or combinations thereof. Exemplary premixes of bensulfuron or an agriculturally acceptable salt or ester thereof and an additive that are or have been commercially available include, but are not limited to LONG GENG® (a premix incorporating acetochlor Shanghai Agro-Chemical Industry Co., Ltd.), KA CAOTE® (a premix incorporating clopyralid by Nanjing Red Sun Co., Ltd.), ZARK D® (a premix incorporating daimuron and mefenacet), INNOVA® (a premix incorporating fentrazamide by Bayer CropScience), MANSOKUM® (a premix incorporating mefenacet by Bayer CropScience), TIAN CAO LINGO (a premix incorporating mefenacet by Shanghai Agro-Chemical Industry Co., Ltd.), YI DA® (a premix incorporating mefenacet by Nanjing Red Sun Co., Ltd.), ZARK® (a premix incorporating mefenacet), WOLF ACE® (a premix incorporating mefenacet and thiobencarb by Kumiai Chemical Industry Co., Ltd.), DUET DF® and DUET® (premixes incorporating propanil by RiceCo LLC), and XIN HE BAO® (a premix incorporating thiobencarb by Shanghai Agro-Chemical Industry Co., Ltd.).

In some embodiments, the additive includes an agriculturally acceptable adjuvant. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, microcapsules or wettable powders, or liquids, such as, for example, emulsifiable concentrates, solutions, emulsions or suspensions. They can also be provided as a pre-mix or tank mixed. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)) or less; nonylphenol ethoxylate or less; benzylcocoalkyldimethyl quaternary ammonium salt or less; blend of petroleum hydrocarbon, alkyl esters, organic acid, and anionic surfactant or less; $C_9$-$C_{11}$ alkylpolyglycoside or less; phosphate alcohol ethoxylate or less; natural primary alcohol ($C_{12}$-$C_{16}$) ethoxylate or less; di-sec-butylphenol EO-PO block copolymer or less; polysiloxane-methyl cap or less; nonylphenol ethoxylate+urea ammonium nitrate or less; emulsified methylated seed oil or less; tridecyl alcohol (synthetic) ethoxylate (8 EO) or less; tallow amine ethoxylate (15 EO) or less; and PEG(400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, 829148, and N-phenyl-sulfonylbenzoic acid amides, as well as agriculturally acceptable salts thereof and, provided they have a carboxyl group, their agriculturally acceptable derivatives. In some embodiments, the safener can be cloquintocet or an ester or salt thereof, such as cloquintocet (mexyl). In some embodiments, the safener can be dichlormid. In some embodiments, the safener is employed in rice, cereal, corn, or maize. For example, dichlormid or cloquintocet can be used to antagonize harmful effects of the compositions on rice, row crops, and cereals.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivatives, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less; esters of the above vegetable oils or less; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less; esters of mono-, di- and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In formulations designed to be employed as concentrates, (a) and (b) can be present in a concentration of from 0.1 to 98 weight percent (0.5 to 90 weight percent), based on the total weight of the formulation. Concentrates can be diluted with an inert carrier, such as water, prior to application. The diluted formulations applied to undesired vegetation or the locus of undesired vegetation can contain from 0.0006 to 8.0 weight percent of (a) and (b) (e.g., from 0.001 to 5.0 weight percent), based on the total weight of the diluted formulation.

In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

IV. Methods of Application

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation). The compositions can be applied as an in-water application (e.g., to a flooded rice paddy or body of water).

When the compositions are used in crops, the compositions can be applied after seeding and before or after the emergence of the crop plants. In some embodiments, the compositions disclosed herein show good crop tolerance even when the crop has already emerged and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applied to soil or water to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha or from 100 to 500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by).

In some embodiments, herbicidal activity is exhibited by the compounds of the synergistic mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action. In some cases, the compositions are applied to relatively immature undesirable vegetation.

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, rice, vineyards, orchards, perennial plantation crops, corn, cereals, sorghum, soybeans, cotton, sunflower, oilseed rape/canola, sugar beets, turf, or combinations thereof.

In some embodiments, the undesirable vegetation is controlled in rice, vineyards, orchards, perennial plantation crops, corn, cereals, sorghum, soybeans, cotton, sunflower, oilseed rape/canola, sugar beets, turf, or combinations thereof. In some embodiments, the undesirable vegetation is controlled in rice, vineyards, orchards, corn, cereals, sorghum, soybeans, cotton, sunflower, oilseed rape/canola, sugar beets, turf, or combinations thereof.

In some embodiments, the undesirable vegetation is controlled in a row crop (e.g., corn, sorghum, soybean, cotton, or oilseed rape/canola). In certain embodiments, the compositions and methods disclosed herein can be used for controlling undesired vegetation in corn. In certain embodiments, the compositions and methods disclosed herein can be used for controlling undesired vegetation in sorghum. In certain embodiments, the compositions and methods provided herein are utilized to control undesirable vegetation in rice (e.g., direct-seeded, water-seeded, or transplanted rice). In some embodiments, the crop is not pineapple. In some embodiments, the undesirable vegetation is controlled in a perennial plantation crop that is not pineapple, such as cocoa, palm, rubber, coffee, or banana.

The compositions and methods disclosed herein can be used for controlling undesired vegetation in non-crop areas. Exemplary non-crop areas include, but are not limited to, turfgrass, pastures, grasslands, rangelands, fallow land, rights-of-way, aquatic settings, tree and vine, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding. Exemplary resistant crops include, but are not limited to, crops that are resistant to synthetic auxins, or crop plants that, owing to introduction of the gene for *Bacillus thuringiensis* (or Bt) toxin by genetic modification, are resistant to attack by certain insects. In some embodiments, the compositions and methods described herein also can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant crops possessing single, multiple or stacked traits conferring tolerance to single or multiple chemistries and/or single or multiple modes of action. In some embodiments, the undesirable vegetation can be controlled in a crop that is ACCase-tolerant, ALS-tolerant, or a combination thereof. The combination of (a), (b), and a complementary herbicide or salt or ester thereof can be used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or as sequential applications.

In some embodiments, the undesirable vegetation is controlled in rice that is resistant to, for instance, herbicides, pathogens, and/or insects. In certain embodiments, the undesirable vegetation is controlled in rice engineered to express an aryloxyalkanoate dioxygenase (AAD) enzyme to confer herbicidal resistance. For example, in some embodiments, the undesirable vegetation is controlled in AAD-1 rice or AAD-12 rice.

The herbicidal compositions prepared disclosed herein are effective against a variety of types of undesirable vegetation. In some embodiments, the compositions disclosed herein can be used for controlling broadleaf weeds, grass weeds, sedge weeds, and combinations thereof.

In some embodiments, the compositions provided herein are utilized to control undesirable vegetation in rice. In certain embodiments, the undesirable vegetation is *Oryza sativa* (red rice or wild rice, ORYSS), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonurn* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (small flower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SCPJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMMCO), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops. In certain embodiments, the undesirable vegetation is *Oryza sativa*, (volunteer and/or red rice, ORYSS), *Triticum* spp. (volunteer wheat, barley and/or oats), *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crusgalli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

The compositions and methods provided herein can be used to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

In some embodiments, the compositions and methods provided herein are utilized to control undesirable vegetation comprising grass, broadleaf and sedge weeds. In some embodiments, the compositions and methods provided herein are utilized to control undesirable vegetation consisting of grass, broadleaf and sedge weeds. In certain embodiments, the compositions and methods provided herein are utilized to control undesirable grass, broadleaf and sedge vegetation including but not limited to *Chenopodium, Cyperus, Echinochloa, Eleusine, Leptochloa* and *Monochoria.*

In certain cases, the undesirable vegetation is selected from common lambsquarters (*Chenopodium album*), monochoria (*Monochoria vaginalis*), small flower flatsedge (*Cyperus difformis*), Chinese sprangletop (*Leptochloa chinensis*), crabgrass (*Digitaria horizontalis*), rice flatsedge (*Cyperus iria*), itch grass (*Rottboellia exaltata*), or bullgrass (*Eleusine indica*), or combinations thereof. In certain embodiments, the undesirable vegetation can include *Echinochloa crus-galli* grass weeds (e.g., ALS-resistant and ACCase-resistant *Echinochloa* grass weeds, barnyardgrass, etc.). In some embodiments, the undesirable vegetation includes red rice. In some embodiments, the red rice is resistant to ALS herbicides, ACCase herbicides, glyphosate and/or glufosinate.

By way of non-limiting illustration, examples of certain embodiments of the present disclosure are given below.

EXAMPLES

Example 1

Evaluation of Applications of Haloxyfop and ALS Herbicides for Synergistic Weed Control Field trials were conducted in Taiwan, China and Colombia with applications made in the area of naturally occurring weed populations. All treatments were applied using a randomized complete block trial design, with 3 to 4 replications per treatment. Plot size varied and was 1-6 meters× 2-12 meters (width×length). Rice was seeded into the plots, and the rice crop was maintained as a normal commercial crop with appropriate fertilizer and maintenance treatments as needed. Rice size at application varied from the 2 to 4 leaf stage, and weeds were at the 2 to 5 leaf stage. All treatments were foliar applied as post-emergence treatments using backpack sprayers with compressed air or carbon dioxide ($CO_2$) propellant. Spray pressure varied from 25 to 35 pounds per square inch (psi). Spray nozzles used were flat fan, with 1 to 4 nozzle booms used to apply from 200 to 450 L/ha of water as spray diluent. All treatments were mixed in water at appropriately formulated product rates to achieve the desired rates as shown based on a unit area of application (hectare). Commercially available products were used to make all applications, consisting of FENCER® 25OD and BENGALA® 25OD (25 grams active ingredient per liter (g ai/L) penoxsulam in an oil dispersion formulation); GALLANT™ SUPER and VERDICT™ SUPER EC (108 g ai/L haloxyfop-R-methyl in an emulsifiable concentrate formulation); GULLIVER® (500 grams active ingredient per kilograms (g ai/kg) WP (wettable powder)) and NOMINEE® SL (100 g ai/L bispyribac-sodium wettable powder).

Treatments consisted of haloxyfop-R-methyl and an ALS mode of action herbicide (penoxsulam, bispyribac-sodium, bensulfuron-methyl, or azimsulfuron), applied alone or in combination.

The treated plots and control plots were rated blind at various intervals after application. Ratings were based on a scale of 0-100%, as discussed above, wherein 0% indicates complete growth of the undesired vegetation and 100% indicates complete prevention of the undesired vegetation.

Colby's equation was used to determine the herbicidal effects expected from the mixtures, as described above. The results were measured at the evaluation intervals provided in Tables 1-5 after the first application of the compositions. All of the trials exhibited unexpected synergy, and those results were found statistically significant under the p-value test. The combinations tested, application rates and ratios employed, plant species tested, and results are included in Tables 1-5 below.

Colby's equation was used to determine the herbicidal effects expected from the mixtures (S. R. Colby, *Calculating Synergistic and Antagonistic Responses of Herbicide Combinations*, WEEDS 15, p. 22 (1967)). A t-test (alpha=0.05) between Colby predictions and observed combinations was used to test for significant differences indicating synergy or antagonism using replicate data. The results presented in Tables 1-5 were significant according to the described criteria.

TABLE 1

Synergistic Activity of Foliar-Applied Haloxyfop-Methyl and Penoxsulam Evaluated at 7 to 14 DAA (Days After Application) in Rice.

| | | Haloxyfop-methyl (R) | | Penoxsulam | | Haloxyfop-methyl (R) + Penoxsulam | |
|---|---|---|---|---|---|---|---|
| | | | | | | Measured | Colby predicted |
| Weed Bayer | Evaluation Interval | g ai/ha | Mean % weed control | g ai/ha | Mean % weed control | mean % weed control | mean % weed control |
| DIGHO | 7 DAA | 4 | 10.0 | 16 | 0.0 | 51.7 | 10.0 |
| DIGHO | 7 DAA | 4 | 5.0 | 32 | 10.0 | 50.0 | 15.0 |
| DIGHO | 7 DAA | 4 | 5.0 | 8 | 0.0 | 55.0 | 5.0 |
| DIGHO | 7 DAA | 8 | 71.7 | 32 | 6.7 | 93.7 | 73.3 |
| DIGHO | 7 DAA | 8 | 71.7 | 16 | 0.0 | 97.7 | 71.7 |
| CYPIR | 7 DAA | 16 | 0.0 | 32 | 87.0 | 98.0 | 87.0 |
| CYPIR | 7 DAA | 16 | 0.0 | 8 | 62.0 | 93.3 | 62.0 |
| CYPIR | 7 DAA | 8 | 0.0 | 8 | 62.0 | 92.0 | 62.0 |
| ROOEX | 7 DAA | 16 | 75.0 | 16 | 12.5 | 97.0 | 78.5 |
| ROOEX | 7 DAA | 8 | 11.7 | 32 | 3.3 | 85.0 | 14.8 |
| ROOEX | 7 DAA | 8 | 11.7 | 16 | 8.3 | 89.3 | 19.5 |
| ROOEX | 7 DAA | 16 | 66.7 | 32 | 3.3 | 99.7 | 68.3 |
| ELEIN | 7 DAA | 4 | 21.7 | 16 | 0.0 | 98.3 | 21.7 |
| ELEIN | 7 DAA | 4 | 21.7 | 32 | 0.0 | 99.3 | 21.7 |
| ELEIN | 7 DAA | 4 | 21.7 | 8 | 0.0 | 97.0 | 21.7 |
| ECHCG | 7 DAA | 27 | 0.0 | 15 | 95.7 | 100.0 | 95.7 |

TABLE 1-continued

Synergistic Activity of Foliar-Applied Haloxyfop-Methyl and Penoxsulam Evaluated at 7 to 14 DAA (Days After Application) in Rice.

| Weed Bayer | Evaluation Interval | Haloxyfop-methyl (R) | | Penoxsulam | | Haloxyfop-methyl (R) + Penoxsulam | |
|---|---|---|---|---|---|---|---|
| | | g ai/ha | Mean % weed control | g ai/ha | Mean % weed control | Measured mean % weed control | Colby predicted mean % weed control |
| MOOVA | 7 DAA | 16 | 0.0 | 5 | 90.0 | 96.0 | 90.0 |
| ECHCG | 7 DAA | 8 | 0.0 | 10 | 63.3 | 86.7 | 63.3 |
| LEFCH | 7 DAA | 8 | 0.0 | 10 | 0.0 | 73.3 | 0.0 |
| LEFCH | 7 DAA | 8 | 0.0 | 20 | 0.0 | 85.0 | 0.0 |
| LEFCH | 7 DAA | 8 | 0.0 | 30 | 0.0 | 85.0 | 0.0 |
| CYPDI | 14 DAA | 16 | 0.0 | 10 | 93.3 | 98.7 | 93.3 |
| CYPDI | 14 DAA | 32 | 0.0 | 10 | 93.3 | 99.0 | 93.3 |
| LEFCH | 14 DAA | 2 | 0.0 | 30 | 0.0 | 60.0 | 0.0 |
| LEFCH | 14 DAA | 4 | 0.0 | 30 | 0.0 | 90.0 | 0.0 |
| LEFCH | 14 DAA | 8 | 0.0 | 10 | 0.0 | 83.3 | 0.0 |
| LEFCH | 14 DAA | 8 | 0.0 | 20 | 0.0 | 88.3 | 0.0 |
| LEFCH | 14 DAA | 8 | 0.0 | 30 | 0.0 | 94.7 | 0.0 |

Percent Visual Weed Control = 0-100 scale, where 0 = no control and 100 = complete control.
CYPIR = rice flatsedge, *Cyperus iria*
MOOVA = monochoria, *Monochoria vaginalis*
DIGHO = crabgrass, *Digitaria horizontalis*
ECHCG = barnyardgrass, *Echinochloa crus-galli*
ELEIN = bullgrass, *Eleusine indica*
LEFCH = Chinese sprangletop, *Leptochloa chinensis*
ROOEX = itch grass, *Rottboellia exaltata*
g ai/ha = grams active ingredient per hectare

TABLE 2

Synergistic Activity of Foliar-Applied Haloxyfop-Methyl and Penoxsulam Evaluated at 7 to 14 DAA (Days After Application) in Rice.

| Weed Bayer | Evaluation Interval | Haloxyfop-methyl (R) | | Penoxsulam | | Haloxyfop-methyl (R) + Penoxsulam | |
|---|---|---|---|---|---|---|---|
| | | g ai/ha | Mean % weed control | g ai/ha | Mean % weed control | Measured mean % weed control | Colby predicted mean % weed control |
| DIGHO | 15 DAA | 4 | 35.0 | 16 | 0.0 | 100.0 | 35.0 |
| DIGHO | 15 DAA | 8 | 68.3 | 16 | 0.0 | 100.0 | 68.3 |
| DIGHO | 15 DAA | 8 | 68.3 | 32 | 0.0 | 100.0 | 68.3 |
| DIGHO | 15 DAA | 8 | 72.5 | 8 | 0.0 | 99.0 | 72.5 |
| CYPIR | 15 DAA | 16 | 11.3 | 8 | 85.0 | 97.5 | 87.1 |
| CYPIR | 15 DAA | 8 | 0.0 | 8 | 85.0 | 95.3 | 85.0 |
| ROOEX | 15 DAA | 16 | 77.5 | 16 | 12.5 | 99.0 | 81.3 |
| ROOEX | 15 DAA | 4 | 0.0 | 32 | 10.0 | 80.0 | 10.0 |
| ROOEX | 15 DAA | 8 | 6.7 | 8 | 0.0 | 91.3 | 6.7 |
| ROOEX | 15 DAA | 8 | 5.0 | 16 | 8.8 | 99.8 | 13.8 |
| ROOEX | 15 DAA | 8 | 5.0 | 32 | 12.5 | 96.3 | 16.5 |
| ECHCG | 21 DAA | 27 | 0.0 | 15 | 93.3 | 98.3 | 93.3 |
| ROOEX | 28 DAA | 4 | 0.0 | 32 | 10.0 | 85.0 | 10.0 |
| ROOEX | 28 DAA | 8 | 10.0 | 8 | 0.0 | 86.7 | 10.0 |
| ROOEX | 28 DAA | 8 | 7.5 | 16 | 12.5 | 99.5 | 20.0 |
| ROOEX | 28 DAA | 8 | 7.5 | 32 | 12.5 | 96.0 | 18.5 |
| ECHCG | 28 DAA | 13.5 | 0.0 | 30 | 98.3 | 100.0 | 98.3 |
| ECHCG | 28 DAA | 27 | 0.0 | 15 | 91.7 | 98.3 | 91.7 |
| ECHCG | 28 DAA | 27 | 0.0 | 7.5 | 53.3 | 80.0 | 53.3 |
| ECHCG | 28 DAA | 4 | 0.0 | 10 | 56.7 | 86.7 | 56.7 |

TABLE 2-continued

Synergistic Activity of Foliar-Applied Haloxyfop-Methyl and Penoxsulam Evaluated at 7 to 14 DAA (Days After Application) in Rice.

| Weed Bayer | Evaluation Interval | Haloxyfop-methyl (R) | | Penoxsulam | | Haloxyfop-methyl (R) + Penoxsulam | |
|---|---|---|---|---|---|---|---|
| | | g ai/ha | Mean % weed control | g ai/ha | Mean % weed control | Measured mean % weed control | Colby predicted mean % weed control |
| ECHCG | 28 DAA | 8 | 0.0 | 10 | 56.7 | 93.3 | 56.7 |
| LEFCH | 28 DAA | 8 | 0.0 | 30 | 0.0 | 98.0 | 0.0 |

Percent Visual Weed Control = 0-100 scale, where 0 = no control and 100 = complete control.
CYPIR = rice flatsedge, *Cyperus iria*
DIGHO = crabgrass, *Digitaria horizontalis*
ECHCG = barnyardgrass, *Echinochloa crus-galli*
LEFCH = Chinese sprangletop, *Leptochloa chinensis*
ROOEX = itch grass, *Rottboellia exaltata*
g ai/ha = grams active ingredient per hectare

TABLE 3

Synergistic Activity of Foliar-Applied Haloxyfop-Methyl and Bispyribac-Sodium Evaluated at 7 to 28 DAA (Days After Application) in Rice.

| Weed Bayer | Evaluation Interval | Haloxyfop-methyl (R) | | Bispyribac-Sodium | | Bispyribac-Sodium + Haloxyfop-methyl | |
|---|---|---|---|---|---|---|---|
| | | g ai/ha | Mean % weed control | g ai/ha | Mean % weed control | Measured mean % weed control | Colby predicted mean % weed control |
| ECHCG | 7 DAA | 4 | 0.0 | 20 | 53.3 | 71.7 | 53.3 |
| ECHCG | 7 DAA | 8 | 0.0 | 20 | 53.3 | 81.7 | 53.3 |
| ECHCG | 7 DAA | 8 | 0.0 | 40 | 76.7 | 88.3 | 76.7 |
| ECHCG | 14 DAA | 8 | 0.0 | 20 | 35.0 | 93.0 | 35.0 |
| ECHCG | 28 DAA | 4 | 0.0 | 20 | 20.0 | 50.0 | 20.0 |
| ECHCG | 28 DAA | 8 | 6.7 | 20 | 20.0 | 71.7 | 25.3 |
| ECHCG | 28 DAA | 8 | 6.7 | 40 | 88.3 | 99.3 | 89.7 |

Percent Visual Weed Control = 0-100 scale, where 0 = no control and 100 = complete control.
ECHCG = barnyardgrass, *Echinochloa crus-galli*
g ai/ha = grams active ingredient per hectare

TABLE 4

Synergistic Activity of Foliar-Applied Haloxyfop-Methyl and Bensulfuron-Methyl Evaluated at 7 to 28 DAA (Days After Application) in Rice.

| Weed (Bayer Code) | Days After Application | Bensulfuron-Methyl | | Haloxyfop-methyl | | Bensulfuron-Methyl + Haloxyfop-methyl | |
|---|---|---|---|---|---|---|---|
| | | g ai/ha | % Visual Weed Control | g ai/ha | % Visual Weed Control | Observed % Visual Weed Control | Colby Predicted % Visual Weed Control |
| CYPDI | 7 DAA | 20 | 92 | 2 | 0 | 96 | 92 |
| CYPDI | 7 DAA | 10 | 90 | 8 | 0 | 95 | 90 |
| ECHCG | 28 DAA | 40 | 23 | 4 | 0 | 33 | 23 |
| ECHCG | 28 DAA | 20 | 0 | 8 | 0 | 7 | 0 |
| ECHCG | 28 DAA | 40 | 23 | 8 | 0 | 33 | 23 |

Percent Visual Weed Control = 0-100 scale, where 0 = no control and 100 = complete control.
CYPDI = small flower flatsedge, *Cyperus difformis*
ECHCG = barnyardgrass, *Echinochloa crus-galli*
g ai/ha = grams active ingredient per hectare

TABLE 5

Synergistic Activity of Foliar-Applied Haloxyfop-Methyl plus Azimsulfuron Evaluated at 7 to 14 DAA (Days After Application) in Rice.

| Weed Bayer | Evaluation Interval | Haloxyfop-methyl (R) | | Azimsulfuron | | Azimsulfuron + Haloxyfop-methyl | |
|---|---|---|---|---|---|---|---|
| | | g ai/ha | Mean % weed control | g ai/ha | Mean % weed control | Measured mean % weed control | Colby predicted mean % weed control |
| ECHCG | 7 DAA | 8 | 0.0 | 40 | 89.0 | 95.0 | 89.0 |
| LEFCH | 14 DAA | 8 | 90.0 | 10 | 0.0 | 98.3 | 90.0 |
| LEFCH | 14 DAA | 8 | 90.0 | 20 | 0.0 | 100.0 | 90.0 |

Percent Visual Weed Control = 0-100 scale, where 0 = no control and 100 = complete control.
ECHCG = barnyardgrass, *Echinochloa crus-galli*
LEFCH = Chinese sprangletop, *Leptochloa chinensis*
g ai/ha = grams active ingredient per hectare The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising a synergistic, herbicidally effective amount of (a) haloxyfop or an agriculturally acceptable salt or ester thereof and (b) penoxsulam or an agriculturally acceptable salt or ester thereof, wherein the composition does not include any additional herbicides.

2. The composition of claim 1, wherein (a) includes haloxyfop-R-methyl.

3. The composition of claim 1, wherein the weight ratio of (a) to (b) is from 1:50 to 100:1.

4. The composition of claim 3, wherein the weight ratio of (a) to (b) is from 1:20 to 6.4:1.

5. The composition of claim 1, wherein the weight ratio of (a) to (b) is from 1:50 to less than 1:2.

6. The composition of claim 1, wherein the weight ratio of (a) to (b) is from 5:2 to 4:1.

7. The composition of claim 1, wherein the weight ratio of (a) to (b) is from 1:8 to 6.4:1.

8. The composition of claim 1, further comprising a herbicidal safener.

9. The composition of claim 1, further comprising an agriculturally acceptable adjuvant or carrier.

10. A method of controlling undesirable vegetation which comprises applying to vegetation or an area adjacent the vegetation or applying to soil or water to control the emergence or growth of vegetation a composition comprising a synergistic, herbicidally effective amount of (a) haloxyfop or an agriculturally acceptable salt or ester thereof and (b) penoxsulam or an agriculturally acceptable salt or ester thereof,
wherein the composition does not include any additional herbicides.

11. The method of claim 10, wherein (a) and (b) are applied postemergence to the undesirable vegetation.

12. The method of claim 10, wherein (a) includes haloxyfop-R-methyl.

13. The method of claim 10, wherein the weight ratio of (a) to (b) is from 1:50 to 100:1.

14. The method of claim 13, wherein the weight ratio of (a) to (b) is from 1:20 to 6.4:1.

15. The method of claim 10, wherein the weight ratio of (a) to (b) is from 1:50 to less than 1:2.

16. The method of claim 10, wherein the weight ratio of (a) to (b) is from 5:2 to 4:1.

17. The method of claim 10 wherein the weight ratio of (a) to (b) is from 1:8 to 6.4:1.

18. The method of claim 10, further comprising applying a herbicidal safener.

19. The method of claim 10, further comprising applying an agriculturally acceptable adjuvant or carrier.

20. The method of claim 10, wherein the undesirable vegetation is controlled in rice, vineyards, orchards, perennial plantation crops, corn, cereals, sorghum, soybeans, cotton, sunflower, oilseed rape/canola, sugar beets, turf, range and pasture, industrial vegetation management (IVM), rights-of-way, or combinations thereof.

21. The method of claim 10, wherein the undesirable vegetation is controlled in rice.

22. The method of claim 10, wherein the undesirable vegetation is controlled in AAD-1 rice.

23. The method of claim 10, wherein the undesirable vegetation is controlled in a crop that is acetyl coenzyme A carboxylase (ACCase)-tolerant, ALS (acetolactate synthase)-tolerant, or a combination thereof.

24. The method of claim 10, wherein the undesirable vegetation includes a broadleaf weed, a grass weed, or a sedge weed.

25. The method of claim 10, wherein the undesirable vegetation includes common lambsquarters, monochoria, barnyardgrass, Chinese sprangletop, small flower flatsedge, *Digitaria horizontalis*, rice flatsedge, or bullgrass.

26. The method of claim 10, wherein the undesirable vegetation includes *Echinochloa* grass weed.

27. The method of claim 26, wherein the *Echinochloa* grass weeds include ALS and/or ACCase resistant *Echinochloa* grass weed.

28. The method of claim 26, wherein the *Echinochloa* grass weed includes barnyardgrass.

29. The method of claim 10, wherein the undesirable vegetation includes red rice/weedy rice.

30. The method of claim 29, wherein the undesirable vegetation includes red rice and/or weedy rice that is resistant to ALS herbicides, ACCase herbicides, propanil, quinclorac, glyphosate and/or glufosinate.

31. The method of claim 10, wherein the undesirable vegetation comprises a herbicide resistant or tolerant weed.

32. The method of claim 31 wherein the resistant or tolerant weed is a biotype with resistance or tolerance to single or multiple herbicides or single or multiple chemical classes, or inhibitors of single or multiple herbicide modes-of-action.

33. The method of claim 32, wherein the resistant or tolerant weed is a biotype resistant or tolerant to acetolactate synthase (ALS) or acetohydroxy acid synthase (AHAS) inhibitors, photosystem II inhibitors, acetyl CoA carboxylase (ACCase) inhibitors, photosystem I inhibitors, 5-enolpyruvyl-shikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, auxinic/phenoxyacetic acid inhibitors, herbicides with multiple modes-of-action, quinclorac or arylaminopropionic acids.

\* \* \* \* \*